(12) United States Patent
Van Brunt et al.

(10) Patent No.: US 8,396,721 B2
(45) Date of Patent: Mar. 12, 2013

(54) COMMUNITY HEALTH SYSTEM

(75) Inventors: Deryk Van Brunt, Ross, CA (US); Marcos Athanasoulis, Brookline, MA (US)

(73) Assignee: Healthy Communities Institute Corporation, Berkeley, CA (US)

( * ) Notice: Subject to any disclaimer, the term of this patent is extended or adjusted under 35 U.S.C. 154(b) by 330 days.

(21) Appl. No.: 12/711,177

(22) Filed: Feb. 23, 2010

(65) Prior Publication Data

US 2010/0217765 A1    Aug. 26, 2010

Related U.S. Application Data

(60) Provisional application No. 61/154,710, filed on Feb. 23, 2009.

(51) Int. Cl.
*G06Q 10/00* (2012.01)
(52) U.S. Cl. .................................. 705/2; 705/3
(58) Field of Classification Search ........................ 705/2
See application file for complete search history.

(56) References Cited

U.S. PATENT DOCUMENTS

| | | | | |
|---|---|---|---|---|
| 5,557,514 | A * | 9/1996 | Seare et al. | 705/2 |
| 7,454,417 | B2 * | 11/2008 | Tong et al. | 1/1 |
| 7,617,115 | B2 * | 11/2009 | McNair | 705/3 |
| 8,000,979 | B2 * | 8/2011 | Blom | 705/2 |
| 2003/0208382 | A1 * | 11/2003 | Westfall | 705/3 |
| 2006/0136410 | A1 * | 6/2006 | Gaussier et al. | 707/5 |
| 2009/0319295 | A1 * | 12/2009 | Kass-Hout et al. | 705/2 |

* cited by examiner

*Primary Examiner* — Robert Morgan
*Assistant Examiner* — Michael Fuelling
(74) *Attorney, Agent, or Firm* — Steven A. Nielsen; Allman & Nielsen, P.C.

(57) ABSTRACT

A system of machines, databases, user interfaces, graphical displays and data input systems produces comparisons of community health conditions, recommendations to achieve community health improvements and other tangible outputs. The creation, selection and evolution of promising health practices and best health practices is facilitated and continuously reported.

8 Claims, 23 Drawing Sheets

Community Snapshot

Community Dashboard
United States >> California >> San Francisco >> 
How are we doing?　Tuberculosis　　Target　　Trend
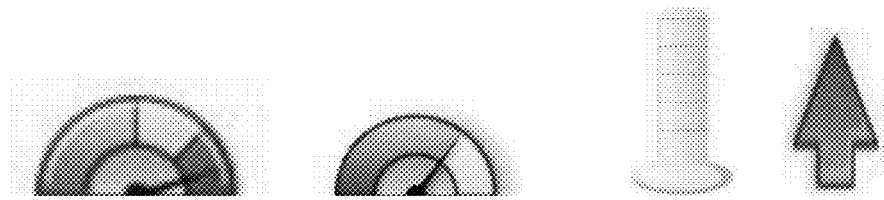
Disparities: 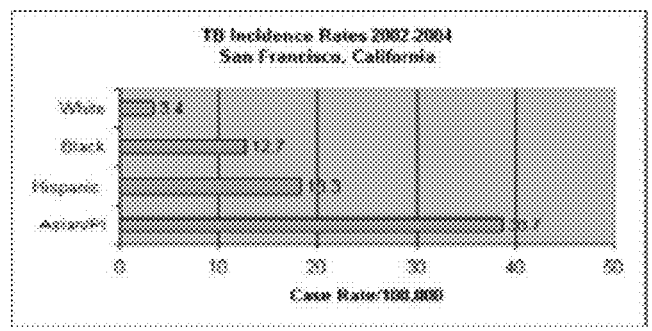
FIG. 2

Community Snapshot

Home > Community Snapshot > Health

Community Snapshot

View the Legend

⊞ Health

▣ Health / Alternative Medicine

▣ Health / An Overview of Mortality Data

▣ Health / Children's Health

▸ Percent Children Without Health Insurance      County : San Francisco 

▸ Percent Children Watching 3+ Hours of Television on Weekdays      County : San Francisco 

▸ Percent of Kindergarteners Immunized      County : San Francisco 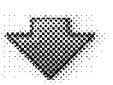

▸ Asthma Rate in Children Age 0-18      County : San Francisco 

FIG. 6

Promising Practices

 Health   Economy   Education

 Natural Environment   Public Safety   Social Environment

 Transportation

[ _____ ] [Search]

Health

- Kaiser Permanente Heart Healthy: Cardiovascular tools and protocols
- Project SWAT (Share the Work to Alleviate the Threat)
- Controlling Asthma in the Richmond Metro Area (CARMA)

More

Education

- Peacemakers Program
- Big Brothers Big Sisters of America
- Adult Basic and Literacy Education (ABLE)

More

Economy

- The Southern Maryland Tri-County Community Action Committee, Inc. (SMTCCAC)
- Resident and Community Services
- Integration of TANF and Child Welfare Systems in El Paso More

Natural Environment

- Landfill Methane Outreach Program (LMOP)
- Flex Your Power Case Study: Glenborough Realty Trust
- Sustainable Design Research Studio

FIG. 7

Home > Promising Practices

Controlling Asthma in the Richmond Metro Area (CARMA)

| | |
|---|---|
| Ranking | Good Idea |
| Description | A collaborative called "Controlling Asthma in the Richmond Metro Area" (CARMA) is working to improve asthma management among urban children up to 18 years of age. To help achieve this ….. |
| Goal / Mission | The goal of this program is to improve asthma management among urban children up to 18 years of age. |
| Results / Accomplishments | This project is expected to help improve community and individual capacity to control asthma, thereby improving the health of those with asthma and decreasing asthma-related medical costs. |
| Categories | Health / Children's Health<br>Health / Chronic Disease<br>Health / Exercise, Nutrition, & Weight |
| Organization(s) | Virginia Department of Health |
| Source | U.S. Department of Health and Human Services: Steps to a Healthier U.S. |
| Date of Publication | 2003 |
| Location | City: Richmond, VA |
| Primary Contact | Virginia Department of Health Division of Child and Adolescent Health<br>1500 East Main Street, Room 137 Richmond, Virginia 23218<br>(804) 786-3694 |

For more details

| | |
|---|---|
| Target Audience | Children |

Back to Promising Practices Home

FIG. 8

Home > Promising Practices

The Medications Management Model

| | |
|---|---|
| Ranking | Evidence-Based Practice |
| Description | Medication-related problems exact a heavy toll on American public health. Indeed, medication errors are a leading cause of death in America. Older adults, ..... |
| Goal / Mission | The goal of this program is to reduce medication-related problems among senior home health patients. |
| Results / Accomplishments | The initial study demonstrated that medication errors can be avoided and prescribing practices can be improved in this vulnerable population. Medication use improved in 50% of intervention patients... |
| Categories | Health / Senior Health<br>Health / Medicine, Drugs, & Medical Technology<br>Health / Health Care Delivery |
| Organization(s) | Partners in Care Foundation |
| Source | National Council on Aging's Center for Healthy Aging |
| Date of Publication | 2006 |
| Geographic Type | Urban |
| Location | City: Burbank, CA |
| Primary Contact | Medications Management Project Partners in Care Foundation 101 S. First Street, Suite 1000 Burbank, CA 91502<br>(818) 526-1780, Ext 180 |
| For more details | |
| Target Audience | Elderly |

Back to Promising Practices Home

FIG. 9

Home

Home > Community Snapshot

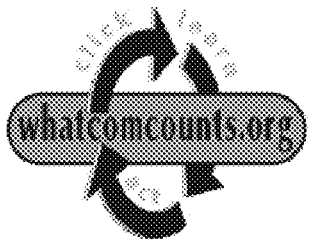

Submit Your Promising Practices

Introduction

Contribute your Promising Practice to WhatcomCounts.org

The purpose of the WhatcomCounts.org Promising Practices database is to inform professionals and community members of successful efforts to create positive change, with the ultimate goal of encouraging implementation of successful practices for the benefit of the local community.

All Promising Practices submitted will be linked to related research and data on WhatcomCounts.org, an independent, nonbiased compilation of information on important community health issues sponsored by the Whatcom Coalition for Healthy Communities.

Give a title to this Promising Practice:

[                                                    ]

What organization(s) or individual runs the program or is responsible for this Promising Practice?

[                                                    ]

What organization(s) or individual runs the program or is responsible for this Promising Practice?

Source of the Promising Practice if different than above (for example, a specific high school may be running a program they got from a national group)

[                                                    ]

Source of the Promising Practice if different than above (for example, a specific high school may be running a program they got from a national group)

[ Next >> ]

FIG. 12

TYPES OF INDICATORS

Legend

| | |
|---|---|
| 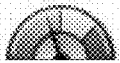 | Compare by Region: This gauge shows how the San Francisco value compares with all counties in the state (or all US counties) |
|  | Compare by Average: This gauge shows how the San Francisco value compares with the median or mean value for all counties in the state (or all US counties). The gauge is blue and white when being higher (or lower) is not necessarily good or bad and is multi-colored when being higher (or lower) is good or bad. |
|  | Compare by Time Period: This gauge shows whether the San Francisco value is increasing or decreasing over time. A green arrow means the value is improving and a red arrow means the value is getting worse. |

FIG. 18

Indicators for San Francisco

| Indicator Name | Topic | Value/Period | Comparison | Trend | Target |
|---|---|---|---|---|---|
| Asthma Rate in Children Age 0-18 | Health/ Child Health | 14.9 per 100 county population under age 18 | Lower Than Other Counties | Stayed the same | Target Not Met |
| Children watching 3+ hours of TV on Weekdays | Health/ Child Health | 25.1 Percent | Higher Than Other Counties | Going Up | Target Not Met |

FIG. 19

Health Action Progress Tracker:
A 2020 Vision for Sonoma County

Click, Learn, Act: The twenty-one indicators presented below show how Sonoma County is measuring up to Health Action's desired community health outcomes.

Health Action Goals and Indicators     Current Target     Status
Sonoma County youth graduate from high school

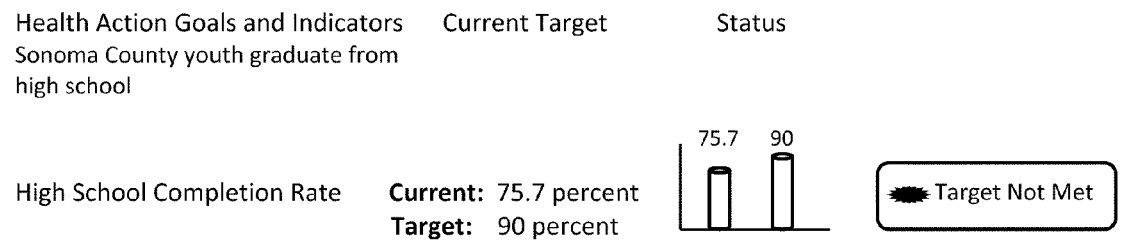

High School Completion Rate     Current: 75.7 percent     Target: 90 percent

FIG. 20

Collaboration Center: Whatcom Asset Building Coalition

The mission of the Whatcom Asset Building Coalition (ABC) is to foster collaboration in the community to increase the financial stability of low-income people in Whatcom County. The Whatcom ABC provides information and outreach to the community about local financial services like budgeting and financial literacy classes, banking institutions, local free tax preparation sites and the Earned Income Tax Credit refund. These services among others are key to keeping families and individuals afloat during financial difficulties as well as providing the necessary means for people to become more self-sufficient.

Goal: Eliminate Poverty
Indicator: Percent of families living below poverty level

On Track

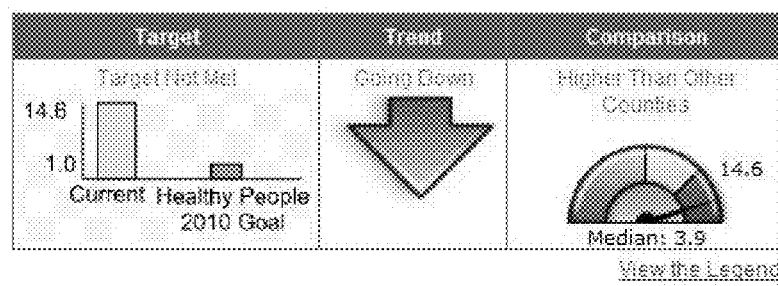

Key Economic Indicators

FIG. 22

Target Icons
Goal ⟹ Community Goal or Other Defined Goal or Target
HP 2010 ⟹ Healthy People 2010 Objectives
HP 2020 ⟹ Healthy People 2020 Objectives
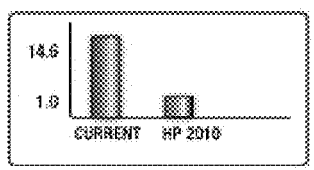
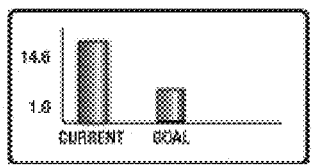
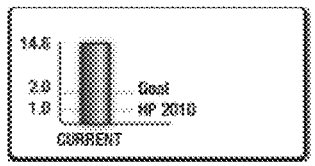
FIG. 24

COMMUNITY HEALTH SYSTEM

CROSS-REFERENCE TO RELATED APPLICATIONS

This is a utility application based upon U.S. patent application Ser. No. 61/154,710 "Community Health System" filed on Feb. 23, 2009. The related application is incorporated herein by reference and is made a part of this application. If any conflict arises between the disclosure of the invention in this utility application and that in the related provisional application, the disclosure in this utility application shall govern. Moreover, the inventors incorporate herein by reference any and all patents, patent applications, and other documents hard copy or electronic, cited or referred to in this application.

BACKGROUND OF THE INVENTION (1) Field of the Invention

The invention generally relates to consumer health information systems. More particularly, the invention relates to means and methods of assisting individuals and communities to evaluate and change health and social conditions.

(2) Description of the Related Art

Various generations of consumer health information (CHI) systems are known in the related art. The first generation of CHI systems was designed to disseminate medical and health information to the public at large. These systems comprised a one-way transmission of medical information, wherein the transmitted information was intended to encourage members of the pubic to take additional steps to solve their perceived problem. This initial CHI systems envisioned consumers having a continued dependence upon health care professionals and health care institutions. The first generation of CHI systems is sometimes labeled "Information and Referral".

The second generation of CHI systems added means for consumers to access and drill down upon larger amounts of relatively static health information. Presenting a selection of health videos on demand is an example of the second generation which is sometimes labeled "Mediated Health Information Systems".

The third generation of CHI systems is sometimes labeled "Personal Health Informational Systems" and comprises electronic health information and decision support assistance. This generation captures and tracks health records for individual consumers and provides customized information for each consumer.

Unfortunately, the related art fails to address the larger issue of providing information regarding specific communities or geographic locations. There is a failure in the known art to consider means of guiding health improvement on a community wide basis. The related art fails to provide or suggest calls to action for areas of interest being examined by a consumer.

The related art comprises a diffuse collection of information that is unintentionally hidden within organizational data collection centers or informational silos. The related art fails to address the needs of small communities to access national data while at the same time providing means for the input and examination of community based data. The related art fails to provide communities the means of understanding and interpreting health and social information in a way that leads to positive changes in behavior and social conditions.

BRIEF SUMMARY OF THE INVENTION

The present invention overcomes shortfalls in the related art by presenting an unobvious departure from the purely individualized approach of prior CHI systems. The present invention discloses unobvious and unique combinations, configurations and presentations of dynamic health information capable of directing and inspiring the improvement of the health of individuals on a community wide basis.

The present invention produces unexpected results on a community wide basis by combining, inter alia, a centralized and normalized database of health and quality of life data with localized templates or interfaces designed to fit the needs of each local community served. In the prior art, valuable data pertaining to local conditions and local resources were prone to rest in organizational silos and thus was unintentionally hidden or not presented in a format easily understood by lay consumers. The present invention overcomes shortfalls in the related art by combining the collective international knowledge of community intervention programs with localized data and providing user friendly graphics to display local trends, data points and target goals while providing useful contextual links to evolving promising practices.

One of the many goals of the disclosed invention is the creation of a database structure and interface system where promising practices may reside and evolve over time and with the input of consumers and health care professionals. The present invention overcomes shortfalls in the prior CHI systems by providing an environment wherein relevant promising practices are presented with data retrieved by a consumer. As a consumer views data points, targets, dashboards or other information, the disclosed invention presents promising practices, calls to action and local resources to help a consumer effect change. When properly implemented the disclosed invention may lead to health and social improvements to an entire community.

The development of promising practices to effect real change gives consumers tangible actions to improve their own quality of life and the collective well being of their community. The operators of the disclosed system introduce promising practices of varying measured success. For example, promising practices may be labeled as good idea, effective practice, evidence based practice or some other descriptive label. As consumers use the presented promising practices, each promising practice may be reassessed and relabeled. Consumers may also be presented with an interface allowing for the submission of proposed promising practices created or located by a consumer.

Information relevant to key words or other queries entered by a content editor may also be presented within adjacent related content columns. The related content columns may feature local resources, indicators, national reports, local reports and promising practices. The content of the related content columns may change on the fly to correlate with the information requested by the consumer.

The invention overcomes shortfalls in the related art in the area of enabling communities to construct informational portals focused upon their communities and with the capacity of viewing additional information on a national or world view. The invention allows small underfunded communities the opportunity to obtain a template to customize and localize to the particular needs of the community. The local template receives information from the main database of the invention. The structure of the main data system feeds a multitude of local templates with data, contextually related links and contextually related promising practices.

Each participating community may access the main system and generate data point and data trend comparisons with other geographical regions. Each local community does not need to duplicate the data collection efforts of the main system These and other objects and advantages will be made apparent when considering the following detailed specification when taken in conjunction with the drawings.

BRIEF DESCRIPTION OF THE DRAWINGS

FIG. 2 is a chart with five types of displays used to convey five types of information related to tuberculosis.

FIG. 6 is a pseudo screen view of a community snapshot of health sorted by topic.

FIG. 7 is a pseudo screen view of a search interface and particular list of promising practices sorted by subject.

FIG. 8 is a pseudo screen view of a promising practice.

FIG. 9 is a pseudo screen view of a promising practice.

FIG. 12 is a pseudo screen view of a user interface designed to accept information regarding promising practices.

FIG. 18 is a legend describing possible meanings to the disclosed gauges and charts.

FIG. 19 shows an alternative embodiment of a composition of comparison, trend and target charts.

FIG. 20 shows an embodiment of a health action progress tracker.

FIG. 22 shows a sample display presenting health and financial status indicators.

FIG. 24 depicts target icons.

DETAILED DESCRIPTION OF EMBODIMENTS OF THE INVENTION

Figure 1:
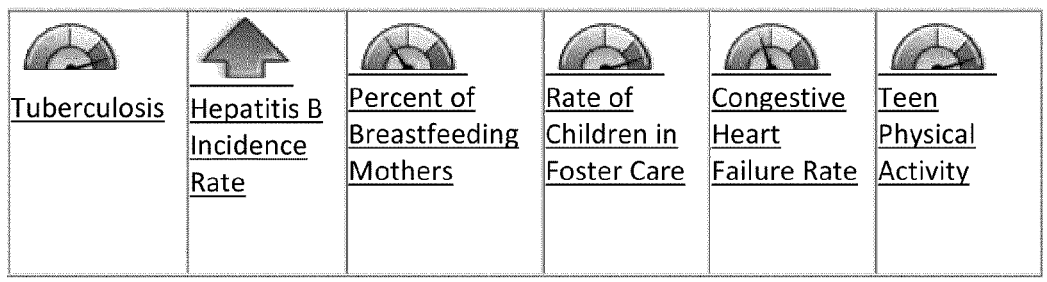
FIG. 1 is a pseudo screen view of a community snapshot showing various dashboard values and a trend indicator.

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all of the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

The following terms are defined herein:

community: a geographical or shared interest subdivision;

data category: a subset of a domain target, data categories may include city, ages, miles driven a week, rates of disease and others;

data element: information or a string of data entered into the database; a data element may be comprised of information belonging to different data categories;

domain target: a relatively broad subject of interest, such as health, education, public safety, transportation, economy, natural environment, social environment and others;

local template: a user interface and data structure used by a community to accept local data and to accept information from the main database.

main database: a series of databases maintained by the operators of the invention, the main database communicates with local templates;

promising practices: a set of instructions or suggestions for action to improve health or social conditions;

related content columns: information presented adjacent to information requested by a consumer, the information presented within a related content column may be updated on the fly to correlate to the information requested by the user.

REFERENCE NUMBERS 100 data element used with an indicator
101 various comparisons between a data element/indicator with other locations 102 tracking of goals
103 tracking of trends
104 visual representations of data elements processed with indicators
200 content and linkages stored within the disclosed system
201 articles or literature available from content and linkages 200
202 documents or facts sheets available from content and linkages 200
203 references to resources and organizations available from content and linkages 200
204 references to events available from content and linkages 200
205 references to people available from content and linkages 200
206 references to on line discussions, volunteer opportunities, and other forms of engagement available from content and linkages 200
207 data processing of content and linkages 200 resulting in the assignment of key words, search strings, and links to related content
300 identification of various practices, such as best practices, promising practices and others
301 summarization of practices
302 ranking of practices
303 categorization of practices and assignments to key words, content search strings, and data domains
400 indicator
401 related content engine for processing of indicators
402 categorization of related information generated from the related content engine 401
403 resulting presentation of information arising from related information 402

The invention may be considered a system and method for evaluating, presenting and changing communities. Communities often have a plethora of data concerning their community but experience difficulty in understanding or interpreting the data. When data is analyzed and interpreted within the related art, the processed information is not tied or linked to information or plans of action that may lead to consumer action. The invention overcomes this shortfall in the art by the disclosed methods of collecting and normalizing data into a format that is easily understood by laypeople and community leaders.

A community, members of a geographic area or interest group may use the invention to study any domain target or broad subject of interest. The users of the invention may gain a greater understanding and potential to influence a domain target by virtue of the system's graphical representations of community comparisons and presentations of calls to action, promising practices and available local resources.

The system allows users to easily understand the data in their community. Users can see how their community is doing compared to other communities, how they are doing over time, and how they are doing as measured against targets and goals. The system presents users with calls to action and resources that can allow action for each data point.

Referring to FIG. 1, a community snapshot is shown with graphical information regarding tuberculosis, hepatitis B incidence rate, percent of breastfeeding mothers, rate of children in foster care, congestive heart failure rate and teen physical activity. Five out of the six subjects are in the form of a dashboard gauge and one subject, hepatitis B incidence rate, is presented in an arrow form, to show a dangerous (red) trend.

Referring to FIG. 2, a chart illustrates five types of displays used for conveying information. A three color dashboard gauge shows tuberculosis (TB) levels within a selected community (San Francisco) to be in a red zone. A two color gauge shows TB to be at the median or mean level as compared to other counties. The thermometer yellow contents at the middle mark shows the level of TB to be in a yellow or warning level as compared to a stated goal level or target level. A red arrow pointed upwardly shows that TB is on an upward trend. The graph shows differences or disparities of TB rates between racial groups.

The graph of FIG. 2 is the end product of storing and tagging information by sub-populations, such as race, ethnicity, income, education, gender and other categories.

The disclosed invention includes the method of:
1. identify data that is statistically valid;
2. identify sub-populations or data categories within the data;
3. identify sub-populations or data categories with data that is statistically valid;
4. store statistically valid data by data sub-populations or data categories;
5. repeat steps 1-4 as information is available and accumulate stored values for each data sub-population or data category; and
6. display or report accumulated values for some or all of the sub-population or data categories.

The accumulated and statistically valid data regarding sub-populations or data categories may be reported in a variety of ways. Such data may be conveyed with tables, charts and/or gauges presented on web pages, presented within web services, presented via transmission to mobile devices or PEDs, (Personal Electronic Devices)

Figure 3:
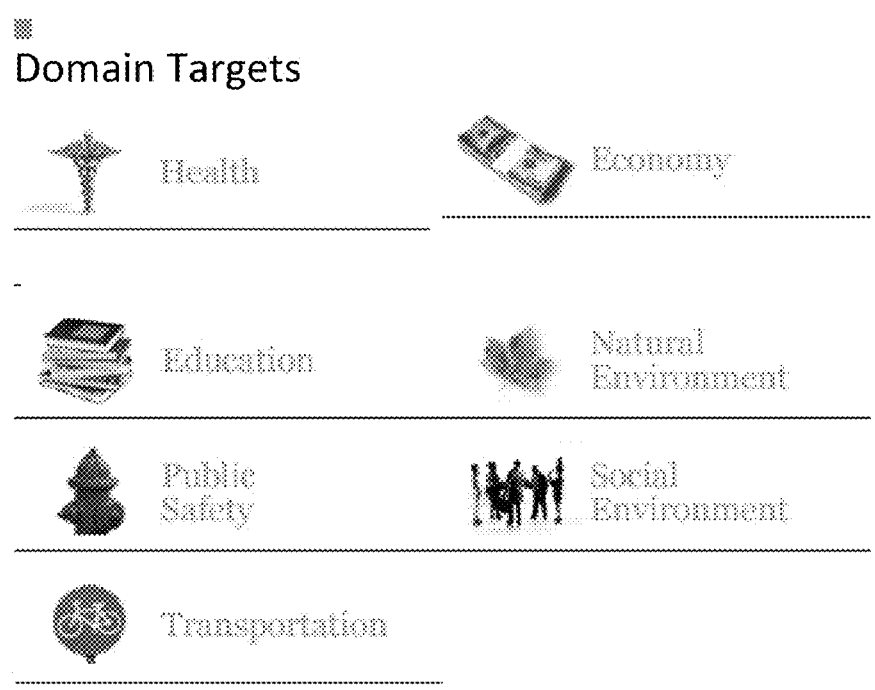
FIG. 3 is a chart of potential domain targets.

Referring to FIG. 3, a group of domain targets are listed and represented with icons.

Figure 4:
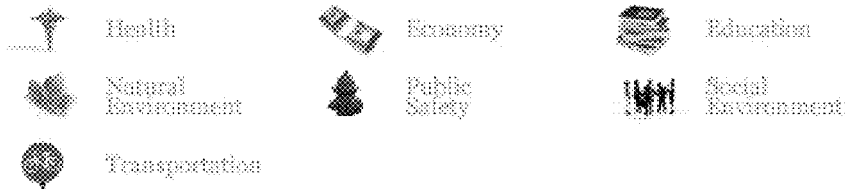
FIG. 4 is a pseudo screen view of a user interface set to display search results by county and by order of topic.

FIG. 4 presents an end user interface for use in searching and sorting by location, topic, subject and/or domain target.

Figure 5:
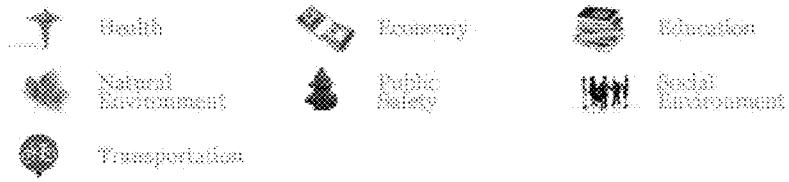
FIG. 5 is a pseudo screen view of a user interface set to display search results by state and by status.

FIG. 5 presents an end user interface for use in searching and sorting by location, topic, subject and/or domain target, wherein sorting by color coded status and by state have been selected.

FIG. 6 presents a pseudo screen view of a community snapshot of health sorted by topic. The community of San Francisco is featured and an arrow icon and dashboard scales are used for a quick visual conveyance of information.

FIG. 7 presents a pseudo screen view of a search interface and particle list of promising practices sorted by subject. Additional practices or promising practices may be found by use of the presented search function.

FIG. 8 is a pseudo screen view of a promising practice defined or ranked as a "Good Idea" and described as, "Controlling Asthma in the Richmond Metro Area (CARMA)." The sample presentation shows a left hand column of information fields such as Goal/Mission; Location; Primary Contact and others.

FIG. 9 is a pseudo screen view of a promising practice defined or ranked as a "Evidence-Based Practice" and described as "The Medications Management Model."

Figure 10:
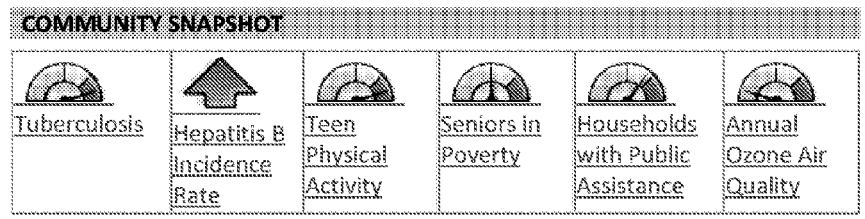
FIG. 10 is a pseudo screen view of a community snapshot featuring a red arrow pointed upwardly to note an increase in hepatitis.

FIG. 10 is a pseudo screen view of a community snapshot featuring a red arrow pointed upwardly to note an increase in hepatitis. FIG. 10 also presents three color dashboard gauges to visually describe rates or levels of tuberculosis, teen physical activity, seniors in poverty, households with public assistance and annual ozone air quality.

Figure 11:
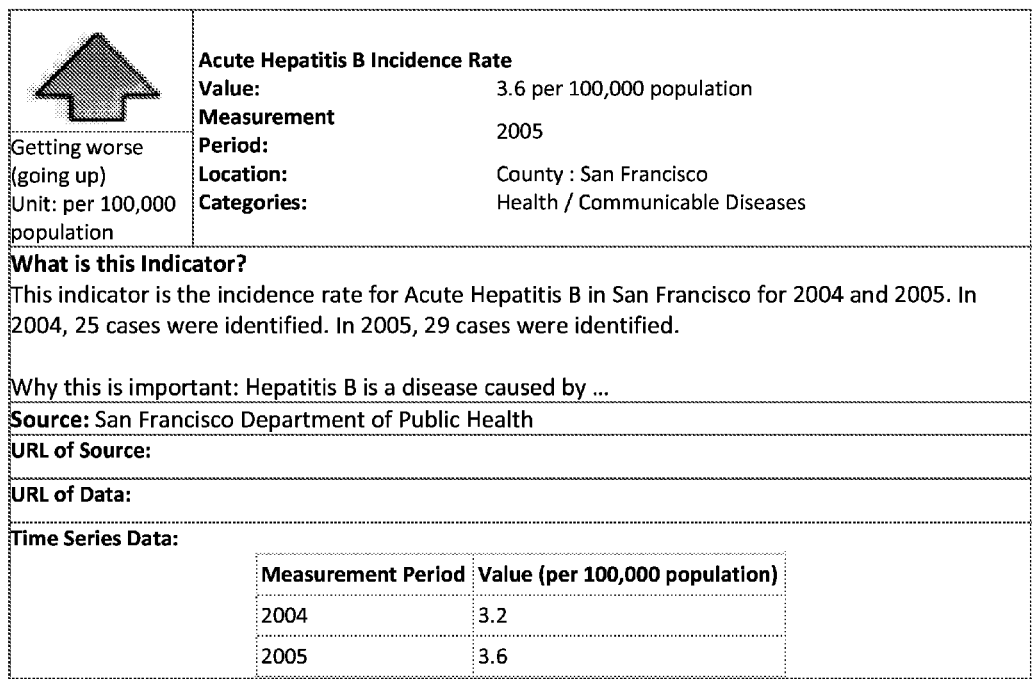
FIG. 11 is a pseudo screen view of a possible presentation of hepatitis information triggered from a hyperlink keyed to hepatitis within FIG. 10.

FIG. 11 presents a pseudo screen view of a possible presentation of hepatitis information triggered from a hyperlink keyed to hepatitis within FIG. 10. Other presentations are contemplated.

FIG. 12 is a pseudo screen view of a user interface designed to accept information regarding promising practices. The ranking of promising practices may be performed by the operators of the system. System owners or contributors may edit and input information presented in numerous categories. FIG. 12 presents a back end interface with means to save input and then present promising practice information to end users by web page, text message, billboard, or other means.

Figure 13:
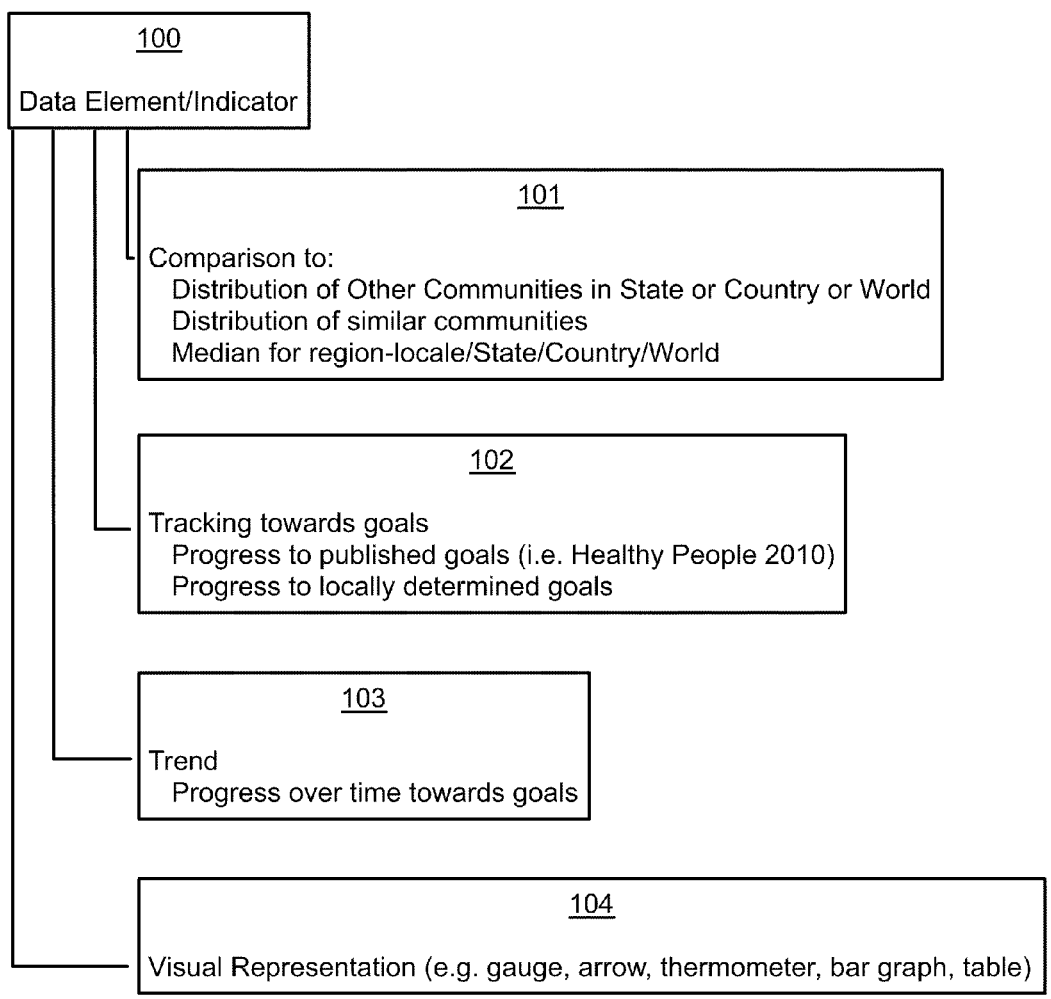
FIG. 13 is a flow chart concerning the flow of information arising from data elements combined with indicators.

FIG. 13 is a flow chart concerning the flow of information arising from data elements combined with indicators. A data element/indicator 100 may result in various comparisons shown in block 101, with include comparisons to: distributions of other communities, distributions of similar communities and medians or averages for communities or locations.

A data element/indicator 100 may result in the display of progress or tracking towards various goals 102, such as progress to published goals or progress to locally determined goals. Trends 103 over time towards goals may be produced from a data element/indicator 101 and various visual representations may also be produced or inspired from a data element/indicator 101.

Figure 14:
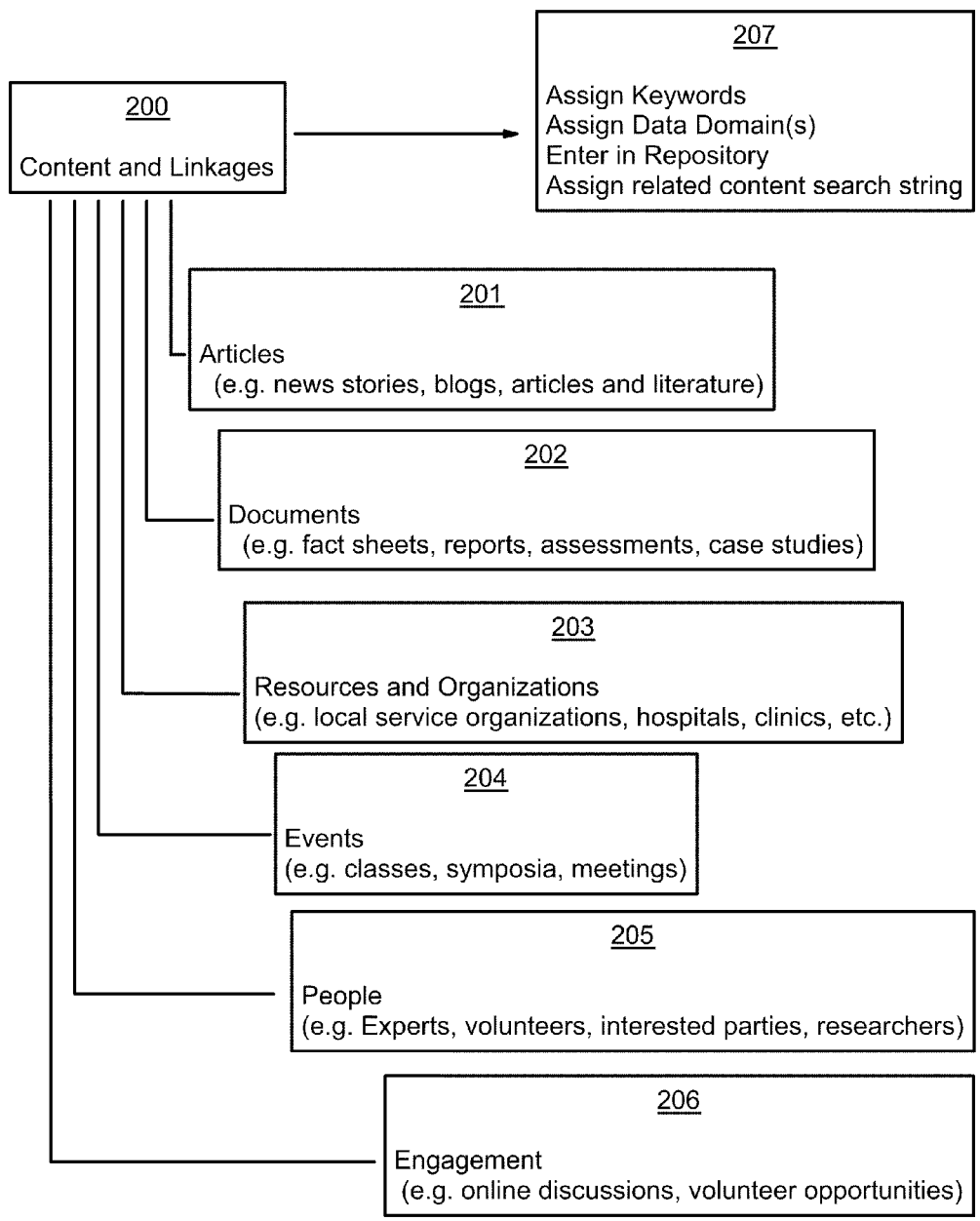
FIG. 14 is a schematic diagram showing results and/or actions arising from content and linkages.

FIG. 14 presents a schematic diagram showing results and/or actions arising from content and linkages 200. Content and linkages 200 from the system may generate articles 201, documents 202, links or references to resources and organizations 203, links or references to events 204, links or references to people 205 and links or references to online discussion groups, volunteer opportunities and other means of personal engagement 206.

From content and linkages 200 various assignments 207 or data labeling may occur. Operators of the system may assign keywords, data domains, search terms or search strings to content and linkages 200. Operators of the system may enter content and linkages 200 and/or data assignments 207 into various databases or data repositories.

Figure 15:
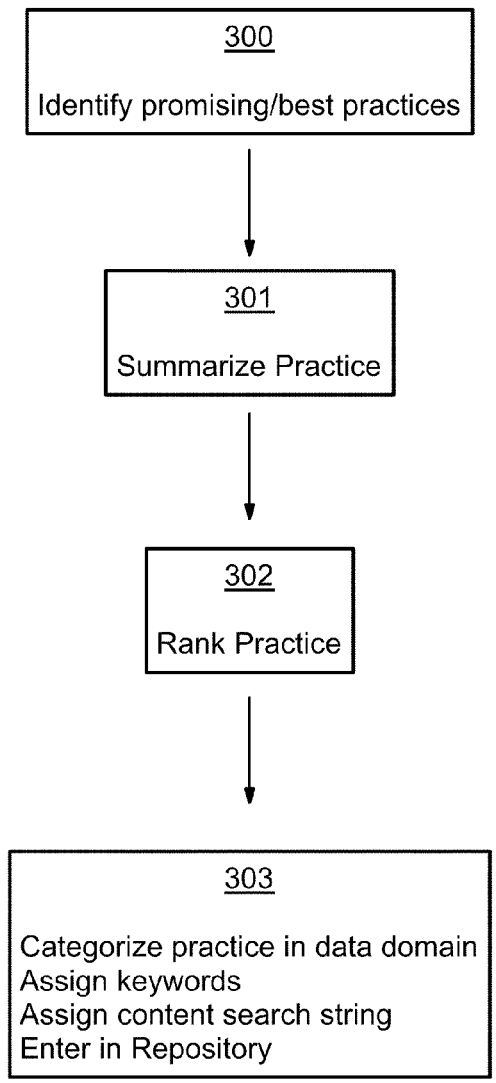
FIG. 15 is a flow chart related to processing of best practices or other types of practices and the identification of such practices.

FIG. 15 presents a possible flow chart showing the processing or evolution of a practice or best practice. Practices may first be identified 300, gathered from operators of the system; or solicited from end users of the system as shown in FIG. 12. A practice may then be summarized 301. Categories of summarization may include a description, goal/mission, results/accomplishments or other categories, including the categories shown on the left hand column of FIG. 9.

Figure 16:
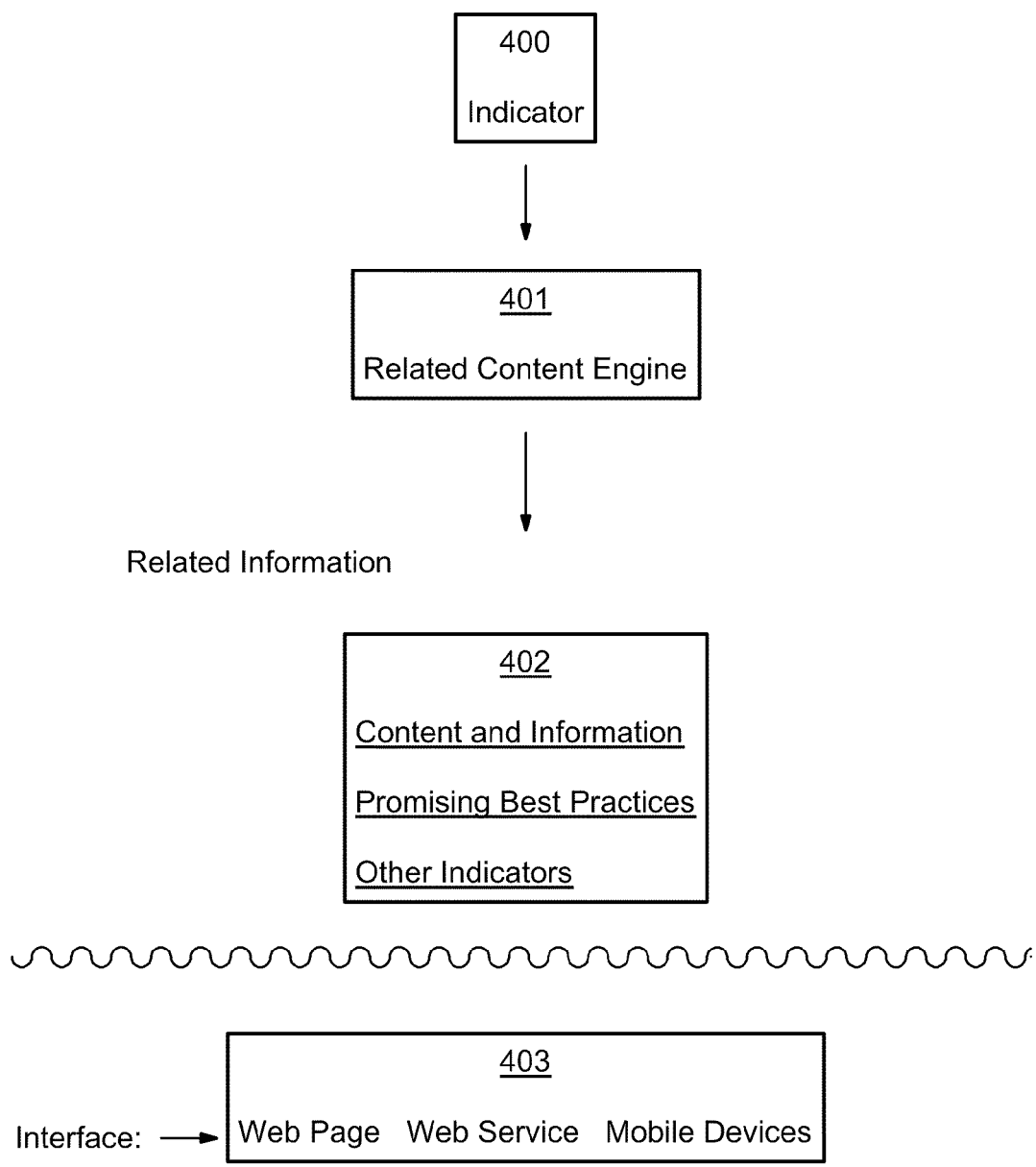
FIG. 16 is a flow chart related to the flow, manipulation and presentation of information processed.

FIG. 16 is a flow chart related to the movement, manipulation and presentation of information processed. An indicator 400 may be used by a related content engine 401 which in turn may assign memory address pointers or otherwise associate an indicator 400 with related information 402. For example, the related content engine 401 may associate an indicator 400 with:

1. Content and information stored within the system;
2. Practices; or
3. Other indicators.

On the user end of the system, an interface 403 may present the information via web page; web service; mobile device or other means.

All embodiments of the disclosed system contemplate the conveyance of information thought web pages, mobile devices, bill boards, and other means.

Figure 17:
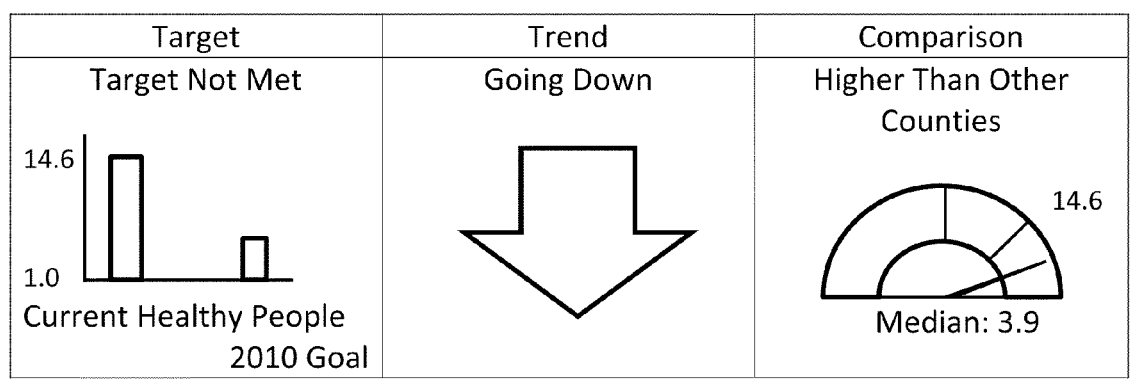
FIG. 17 is a chart of graphical representations showing a target, trend and comparison.

FIG. 17 presents three charts (target, trend and comparison) is a side-by-side manner. This format give a quick and accurate assessment of current health conditions compared to a set goal or target, viewed over time or compared to another geographic location.

FIG. 18 presents a legend of possible gauge embodiments and gauge interpretations. In the presented embodiment, geographic comparisons and are derived by county. Trends or values over time are presented with an arrow.

FIG. 19 shows graphical comparison, trend and target gauges tied to indicators, such as asthma and TV viewing.

FIG. 20 shows another embodiment of presenting a health goal or indicator, a current target value for the health goal or indicator and the current status of reaching a target value.

Figure 21:
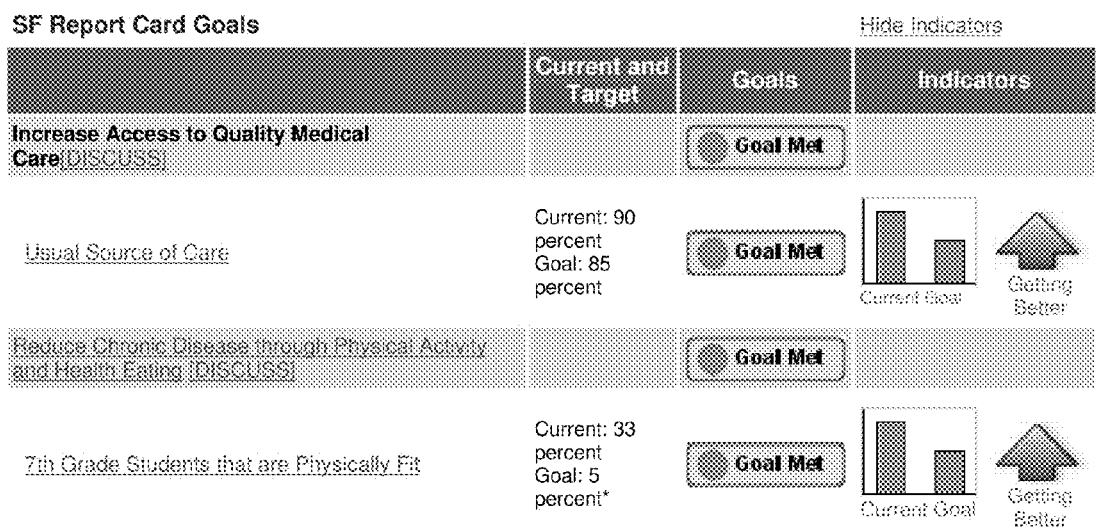
FIG. 21 shows a city report card goal presentation.

FIG. 21 presents a county report card with multiple indicators such as AIDS incidence rates and tuberculosis incidence rates mapped over current value and target value, goal met or unmet, trend over time and bar graphs to show current value vs. goal value.

FIG. 22 is a target, trend and comparison chart that includes an On Track (shown) or Off Track icon. A group of key economic indicators in gauge form is also presented.

Figure 23:
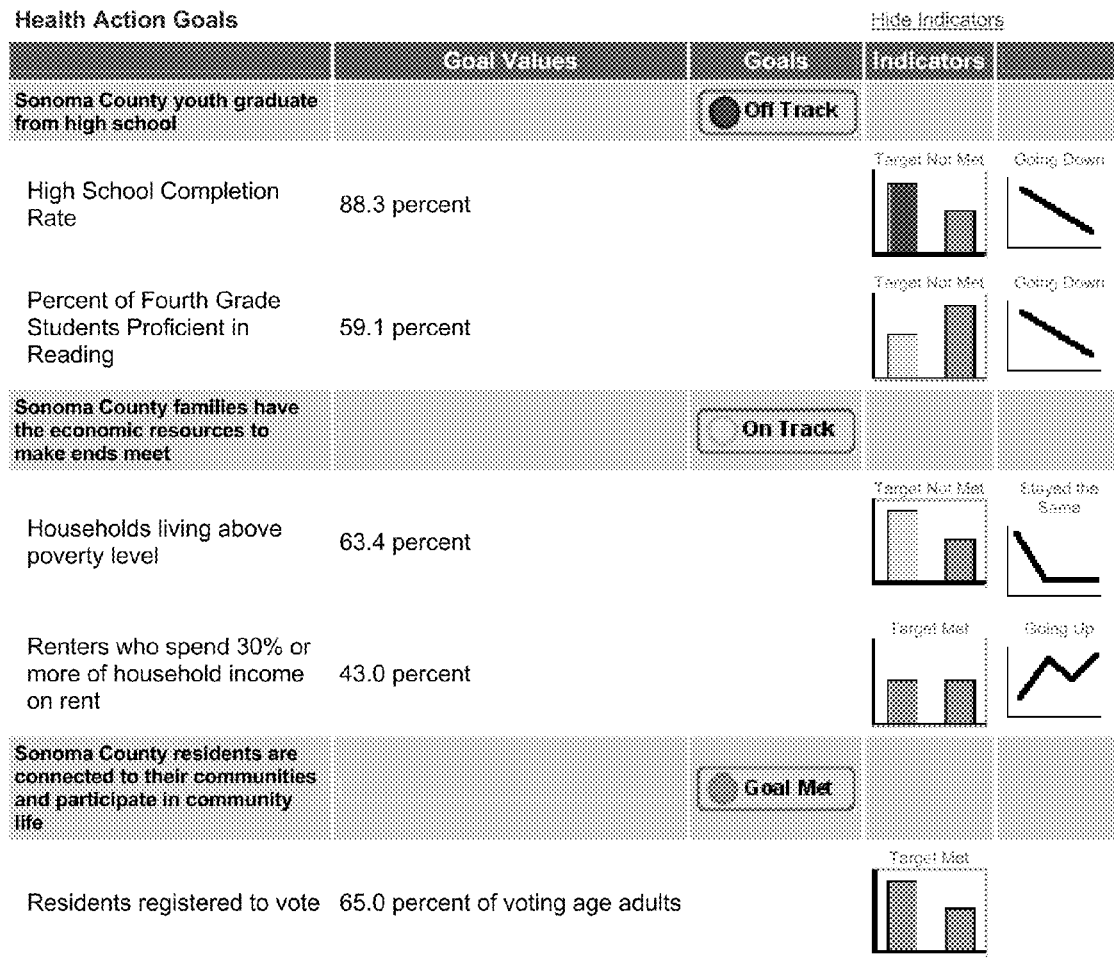
FIG. 23 shows a sample display of health action goals.

FIG. 23 presents health action goals, assigned goal values, an Off Track or On Track icons for current trends, bar graphs to illustrate target values vs. current values and line graphs.

The invention includes the following items:

Item 1: A method of collecting health and quality of life information in a geographic and temporal context, the method comprising the steps of:
a) collecting data elements regarding health and quality of life information pertaining to communities, with the term "community" is defined as a geographical or shared interest subdivision;
b) converting the collected data elements into a canonical form by calculating the percentiles of distribution of all data elements across all available time periods and communities;
c) storing the percentiles of distribution within a database;
d) assigning a target value for each data category of the data elements and storing the target values for each data category in a database;
e) assigning all data categories to one or more target domain subjects;
f) assigning a keyword search text string to each data category and each target domain subject;
g) collecting and summarizing interventions or practices pertaining to the data categories and target domain subjects; and
h) assigning each collected and summarized intervention and practice to a data category and target domain subject.

Item 2: The method of item 1, further comprising the step of assigning a value to represent the rigor of the valuation methods used in evaluating each collected and summarized intervention and practice.

Item 3: The method of item 2, further comprising the step of presenting a visual display which shows a comparison of communities by any data category, the visual displays and/or the underlying information may be presented in web pages, text messages, billboards, mobile devices and other means.

Item 4: the method of item 3, further comprising the step of graphically presenting a comparison of data trends of user selected communities.

Item 5: The method of item 3, further comprising the step of presenting a dashboard graphic to present a comparison of user selected communities.

Item 6: The method of item 3, further comprising the steps of:
a) displaying data changes over a period of time;
b) assigning a normative value to increases and decreases to each data category; and
c) displaying a colored directional arrow for data changes defined as good or a different colored directional arrow for data changes defined as bad.

Item 7: The method of item 3, further comprising the step of displaying a comparison of a data value of a selected data category against the target value assigned to the selected data category.

Item 8: The method of item 3, further comprising the steps of:
a) assigning calls to action for each data category; and
b) presenting calls to action in response to a key word search.

Item 9: The method of item 3, further comprising the step of displaying a collected and summarized intervention and practice in response to a key word search.

Item 10: The method of claim 3, further comprising the steps of:
a) collecting information regarding news, community resources, and events;
b) assigning the collected information to communities;
c) assigning the collected information to target domain subjects; and
d) displaying portions of the collected information in response to a key word search.

While certain aspects of the invention are presented in certain claim forms, the inventors contemplate the various aspects of the invention in any number of claim forms.

What is claimed is:

1. A method of a machine implemented system, the system to manipulate data within a database for the visual display of manipulated data for collecting and presenting health and quality of life information in a geographic and temporal context, the method comprising the steps of:
    a) the system collecting and inputting data elements into a database, the data elements related to health and quality of life information pertaining to communities, with the term "community" is defined as a geographical or shared interest subdivision;
    b) the system converting the collected and inputted data elements into a canonical form by calculating the percentiles of distribution of all data elements across all available time periods and communities;
    c) the system storing the percentiles of distribution within the database;
    d) the system assigning a target value for each data category of the data elements and storing the target values for each data category in the database;
    e) the system assigning all data categories to one or more target domain subjects with each target domain subject entered into the database;
    f) the system assigning a keyword search text string to each data category and each target domain subject and entering said keyword search text string into the database;
    g) the system collecting and summarizing interventions and promising practices pertaining to the data categories and target domain subjects entered into the database;
    h) the system assigning each collected and summarized intervention and promising practice to a data category and target domain subject and entering the assignments into the database;
    i) the system retrieving data from the database to present a visual display showing a comparison of communities by user selected data categories, the data categories retrieved by the system from the database;
    j) the system retrieving data to:
        i) present a visual display presenting data changes mapped over time;
        ii) present a visual display of a first colored directional arrow pointed in a first direction for data changes defined as positive and present a second colored directional arrow pointed in a second direction for data changed defined as negative; and
    k) the system assigning and entering into the database a call to action for each data category and the system retrieving and presenting a call to action in response to a key word search within the database, with the term "call to action" defined as a proposed action to improve a given condition.

2. The method of claim 1 further including the system performing the steps of:
    collecting rank descriptions of promising practices, the rank descriptions comprising:
    i) evidence based practice;
    ii) effective practice; and
    iii) good idea.

3. The method of claim 2 wherein the system retrieves and displays the rank descriptions for promising practices.

4. The method of claim 1, further comprising the step of the system graphically presenting a comparison of data trends of user selected communities.

5. The method of claim 1, further comprising the step of the system presenting a dashboard graphic to present a comparison of user selected communities.

6. The method of claim 1, further comprising the step of the system displaying a comparison of a data value of a selected data category against the target value assigned to the selected data category.

7. The method of claim 1, further comprising the step of the system displaying a collected and summarized intervention and practice in response to a key word search.

8. The method of claim 1, further comprising the steps of the system:
    a) collecting information regarding news, community resources, and events;
    b) assigning the collected information to communities;
    c) assigning the collected information to target domain subjects; and
    c) the system displaying portions of the collected information in response to a key word search.

* * * * *